(12) United States Patent
Dolnik et al.

(10) Patent No.: US 8,449,880 B2
(45) Date of Patent: May 28, 2013

(54) CHEMICAL MODIFICATION OF PROTEINS FOR THEIR MORE ACCURATE MOLECULAR-WEIGHT DETERMINATION BY ELECTROPHORESIS

(76) Inventors: Vladislav Dolnik, Palo Alto, CA (US); William A. Gurske, Fremont, CA (US)

( * ) Notice: Subject to any disclaimer, the term of this patent is extended or adjusted under 35 U.S.C. 154(b) by 194 days.

(21) Appl. No.: 12/952,166

(22) Filed: Nov. 22, 2010

(65) Prior Publication Data

US 2012/0125775 A1 May 24, 2012

(51) Int. Cl.
*G01N 27/447* (2006.01)
*G01N 27/26* (2006.01)

(52) U.S. Cl.
USPC .......... 424/94.3; 530/402; 530/409; 530/410; 204/451; 204/452

(58) Field of Classification Search
None
See application file for complete search history.

(56) References Cited

U.S. PATENT DOCUMENTS 5,370,777 A * 12/1994 Guttman et al. ............. 204/452
7,381,317 B2 * 6/2008 Liu et al. ..................... 204/605
2004/0248127 A1 * 12/2004 Te Kaat et al. .................. 435/6
2010/0187113 A1 * 7/2010 Dolnik ......................... 204/453
2011/0155575 A1 * 6/2011 Dorairaj et al. ............... 204/453

OTHER PUBLICATIONS

Shelburne et al. J. Biol. Chem. Mar. 10, 1974; 249 (5), 1428-1433.*
Eley et al. Analytical biochemistry 1979; 92, 411-419.*
Stark GR. Biochemistry 1965; 4(6), 1030-1036.*
Dolnik et al. Electrophoresis 2011, 32, 2893-2897.*

* cited by examiner

Primary Examiner — Frederick Krass
Assistant Examiner — Thuy Le (57) ABSTRACT

Disclosed herein is a composition and method for sample preparation of proteins for their size separation by electrophoresis, suitable for molecular-weight determination of proteins in the range between about 14,000 and 500,000. In an embodiment, proteins, particularly those exhibiting biased migration, are modified to change their intrinsic charge, or carbohydrate component to improve accuracy of their molecular weights as determined by electrophoretic size separation via their interaction with ionic surfactants. In a preferred embodiment, the proteins are carbamylated with potassium cyanate and their carbohydrate components are oxidized with sodium periodate.

18 Claims, 5 Drawing Sheets

CHEMICAL MODIFICATION OF PROTEINS FOR THEIR MORE ACCURATE MOLECULAR-WEIGHT DETERMINATION BY ELECTROPHORESIS

STATEMENT REGARDING FEDERALLY SPONSORED RESEARCH

The patent application is based on the research sponsored by NIH SBIR grant number 5 R43 GM085935-02.

REFERENCES CITED

U.S. patent Documents:
1) U.S. Pat. No. 4,481,094 Stabilized polyacrylamide gels and system for SDS electrophoresis
2) U.S. Pat. No. 5,089,111 Electrophoretic sieving in gel-free media with dissolved polymers
3) U.S. Pat. No. 5,143,753 Suppression of electroosmosis with hydrolytically stable coatings
4) U.S. Pat. No. 5,213,669 Capillary column containing a dynamically cross-linked composition and method of use
5) U.S. Pat. No. 5,275,708 Cetyltrimethylammonium bromide gel electrophoresis
6) U.S. Pat. No. 5,370,777 Capillary column containing removable separation gel composition and method of use
7) U.S. Pat. No. 5,470,916 Formulations for polyacrylamide matrices in electrokinetic and chromatographic methodologies
8) U.S. Pat. No. 7,799,195 Neutral polysaccharide wall coating for electrophoretic separations in capillaries and microchannels
9) 20020049184 Solution of galactomannans as a sieving matrix in capillary electrophoresis
10) 20050161329 Multiplexed capillary electrophoresis systems
11) 20040050702 Methods and compositions for capillary electrophoresis (CE)
12) 20090314638 Methods and compositions for capillary electrophoresis
13) 2008079217 Capillary sieving electrophoresis with a cationic surfactant for size separation of proteins
14) Ser. No. 12/359,345 Capillary sieving electrophoresis with a cationic surfactant for size separation of proteins

OTHER REFERENCES

[1] Shapiro, A. L., Vinuela, E., Maizel, J. V., Molecular weight estimation of polypeptide chains by electrophoresis in SDS-polyacrylamide gels. *Biochem. Biophys. Res. Commun.* 28, 815-820 (1967).
[2] Shapiro, A. L., Maizel, J. V., Molecular weight estimation of polypeptides by SDS-polyacrylamide gel electrophoresis: further data concerning resolving power and general considerations. *Anal. Biochem.* 29, 505-514 (1969).
[3] Weber, K., Osborn, M., The Reliability of Molecular Weight Determinations by Dodecyl Sulfate-Polyacrylamide Gel Electrophoresis. *J. Biol. Chem.* 242, 4406-4412 (1969).
[4] Dunker, A. K., Rueckert, R. R., Observations on molecular weight determinations on polyacrylamide gel. *J. Biol. Chem.* 244, 5074-5080 (1969).
[5] Williams, J. G., Gratzer, W. B., Limitations of the detergent polyacrylamide gel electrophoresis method for molecular weight determination of proteins. *J. Chromatogr.* 57, 121-125 (1971).
[6] Nozaki, Y., Reynolds, J. A., Tanford, C., The Interaction of a Cationic Detergent with Bovine Serum Albumin and Other Proteins. *J. Biol. Chem.* 249, 4452-4459 (1974).
[7] Schick, M., Influence of a cationic detergent on electrophoresis in polyacrylamide gel. *Anal. Biochem.* 63, 345-349 (1975).
[8] Akins, R. E., Levin, P. M., Tuan, R. S., Cetyltrimethylammonium bromide discontinuous gel electrophoresis: M(r)-based separation of proteins with retention of enzymatic activity. *Anal. Biochem.* 202, 172-178 (1992).
[9] Akins, R. E., Tuan, R. S., Separation of proteins using cetyltrimethylammonium bromide discontinuous gel electrophoresis. *Mol. Biotech.* 1, 211-228 (1994).
[10] Akin, D. T., Shapira, R., Kinkade Jr., J. M., The determination of molecular weights of biologically active proteins by cetyltrimethylammonium bromide-polyacrylamide gel electrophoresis. *Analytical Biochemistry* 145, 170-176 (1985).
[11] Eley, M. H., Burns, P. C., Kannapell, C. C., Campbell, P. S., Cetyltrimethylammonium bromide polyacrylamide gel electrophoresis: estimation of protein subunit molecular weights using cationic detergents. *Anal. Biochem.* 92, 411-419 (1979).
[12] Panyim, S., Thitipongpanich, R., Supatimusro, D., A simplified gel electrophoretic system and its validity for molecular weight determinations of protein cetyltrimethylammonium complexes. *Anal. Biochem.* 81, 320-327 (1977).
[13] Hjerten, S., High-performance electrophoresis: the electrophoretic counterpart of high-performance liquid chromatography. *J. Chromatogr.* 270, 1-6 (1983).
[14] Cohen, A. S., Karger, B. L., High-performance sodium dodecyl sulfate polyacrylamide gel capillary electrophoresis of peptides and proteins. *J. Chromatogr.* 397, 409-417 (1987).
[15] Hjerten, S., Valtcheva, L., Elenbring, K., Eaker, D., High-performance electrophoresis of acidic and basic low-molecular-weight compounds and of proteins in the presence of polymers and neutral surfactants. *J. Liq. Chromatogr.* 12, 2471-2499 (1989).
[16] Ganzler, K., Greve, K. S., Cohen, A. S., Karger, B. L., Guttman, A., Cooke, N. C., High-Performance Capillary Electrophoresis of SDS Protein Complexes Using UV-Transparent Polymer Networks. *Anal. Chem.* 64, 2665-2671 (1992).
[17] Sudor, J., Foret, F., Bocek, P., Pressure Refilled Polyacrylamide Columns for the Separation of Oligonucleotides by Capillary Electrophoresis. *Electrophoresis* 12, 056-1058 (1991).
[18] Heiger, D. N., Cohen, A. S., Karger, B. L., Separation of DNA Restriction Fragments by High-Performance Capillary Electrophoresis with Low and Zero Cross-Linked Polyacrylamide Using Continuous and Pulsed Electric-Fields. *J. Chromatogr.* 516, 33-48 (1990).
[19] Smithies, O., Disulfide-bond cleavage and formation in proteins. *Science* 150, 1595-1598 (1965).
[20] Dolnik, V., Gurske, W. A., Padua, A., Galactomannans as a sieving matrix in capillary electrophoresis. *Electrophoresis* 22, 707-719 (2001).
[21] Izumi, T., Yamaguchi, M., Yoneda, K., Isobe, T., Okuyama, T., Shinoda, T., Use of Glucomannan for the Separation of DNA Fragments by Capillary Electrophoresis. *J. Chromatogr. A* 652, 41-46 (1993).
[22] Kleemiss, M. H., Gilges, M., Schomburg, G., Capillary Electrophoresis of DNA Restriction Fragments with Solutions of Entangled Polymers. *Electrophoresis* 19, 224-230 (1998).

[23] Lindberg, P., Righetti, P. G., Gelfi, C., Roeraade, J., Electrophoresis of DNA-Sequencing Fragments at Elevated-Temperature in Capillaries Filled with Poly(N-Acryloylaminopropanol) Gels. *Electrophoresis* 18, 2909-2914 (1997).

[24] Taylor, J. A., Yeung, E. S., Axial-Beam Laser-Excited Fluorescence Detection in Capillary Electrophoresis. *Anal. Chem.* 64, 1741-1744 (1992).

[25] Petersen, S. L., Ballou, N. E., Effects of Capillary Temperature Control and Electrophoretic Heterogeneity on Parameters Characterizing Separations of Particles by Capillary Zone Electrophoresis. *Anal. Chem.* 64, 1676-1681 (1992).

[26] Nakatani, M., Shibukawa, A., Nakagawa, T., Effect of temperature and viscosity of sieving medium on electrophoretic behavior of sodium dodecyl sulfate-proteins on capillary electrophoresis in presence of pullulan. *Electrophoresis* 17, 1210-1213 (1996).

[27] Yao, S., Anex, D. S., Caldwell, W. B., Arnold, D. W., Smith, K. B., Schultz, P. G., SDS capillary gel electrophoresis of proteins in microfabricated channels. *Proc. Natl. Acad. Sci. U.S.A.* 96, 5372-5377 (1999).

[28] Bousse, L., Mouradian, S., Minalla, A., Yee, H., Williams, K., Dubrow, R., Protein sizing on a microchip. *Anal. Chem.* 73, 1207-1212 (2001).

[29] Cannon-Carlson, S., Tang. J., Modification of the Laemmli Sodium Dodecyl Sulfate-Polyacrylamide Gel Electrophoresis Procedure to Eliminate Artifacts on Reducing and Nonreducing Gels. *Anal. Biochem.* 246, 146-148 (1997).

[30] de Jong, W. W., Zweers, A., Cohen, L. H., Influence of single amino acid substitutions on electrophoretic mobility of sodium dodecyl sulfate-protein complexes. *Biochem. Biophys. Res. Commun.* 82, 532-539 (1978).

[31] Otzen, D. E., Protein Unfolding in detergents: Effect of micelle structures, ionic strength, pH, and temperature. *Biophys. J.* 83, 2219-2230 (2002).

[32] Nelson, C. A., The binding of detergents to proteins. *J. Biol. Chem.* 246, 3895-3901 (1971).

[33] Swank, R. T., Munkres, K. D., Molecular weight analysis of oligopeptides by electrophoresis in polyacrylamide gel with sodium dodecyl sulphate. *Anal. Biochem.* 39, 462-477 (1971).

[34] Guttman, A., Nolan, J., Comparison of the Separation of Proteins by Sodium Dodecyl Sulfate-Slab Gel Electrophoresis and Capillary Sodium Dodecyl Sulfate-Gel Electrophoresis. *Anal. Biochem.* 221, 285-289 (1994).

[35] Werner, W. E., Demorest, D. M., Wiktorowicz, J. E., Automated Ferguson analysis of glycoproteins by capillary electrophoresis using a replaceable sieving matrix. *Electrophoresis* 14, 759-763 (1993).

[36] Guttman, A., Shieh, P., Lindahl, J., Cooke, N., Capillary Sodium Dodecyl Sulfate Gel Electrophoresis of Proteins. II. On the Ferguson method in polyethylene oxide gels. *J. Chromatogr. A* 676, 227-231 (1994).

[37] Kelly, L., Barthmaier, P., Glycoprotein sizing on the Agilent 2100 bioanalyzer. http://www.chem.agilent.com/Library/applications/5989-3336EN_150.pdf

FIELD OF THE INVENTION

The present invention relates to electrophoretic size separation of proteins in sieving media, wherein one or more ionic surfactants form charged complexes with the proteins, equalize their surface charge density, make them migrating in sieving media independently of their intrinsic charge, and allow their size separation and molecular-weight determination. Specifically, the invention is directed to the sample preparation of proteins anomalously migrating in the presence of ionic surfactants, which modifies those anomalously migrating proteins and normalizes their electrophoretic migration.

BACKGROUND OF THE INVENTION

Electrophoresis in Sieving Media

Electrophoretic sieving media are used to size separate biopolymers: nucleic acids, polysaccharides, and proteins. They provide a system of obstacles (typically gel or entangled polymers) in the electrophoretic migration path so that the migrating biopolymers collide with the obstacles and these collisions suppress their apparent migration velocity. (The first electrophoretic sieving media were starch and polyacrylamide gel.) The size separation is based on the fact that the electrophoretic migration of larger molecules and particles is retarded more than that of small molecules. Nucleic acids are equally ionized at non-acidic pH and have sufficient charge and mobility. They need not be modified to size separate during electrophoretic migration in sieving media. On the other hand, protein ionization and charge significantly vary depending on the amino acid composition. Therefore, native proteins are not size separated in sieving media in the absence of ionic surfactants. However, when heated with an ionic surfactant, proteins denature and bind the ionic surfactant, generating complexes with more or less equal surface charge density. These complexes migrate in sieving media according to their size.

Slab Gel Electrophoresis

SDS electrophoresis in polyacrylamide slab gel (SDS PAGE) was the first method separating proteins according to their size[1-4]. Shortly after the invention of SDS PAGE, a method separating proteins by polyacrylamide gel electrophoresis (PAGE) in the presence of cationic surfactants was described[5]. A study observing the migration behavior of protein-cationic-surfactant-complexes followed, predicting a failure of the electrophoresis in the presence of cationic surfactants to determine molecular weights of proteins[6]. Later, cetylpyridinium chloride[7] and cetyltrimethylammonium bromide[8-12] were used for size separations of proteins by PAGE. Several protocols have been developed to denature proteins with cetyltrimethylammonium bromide[8-12].

Capillary Electrophoresis

When electrophoresis of proteins in sieving media was transferred from slab gels into capillaries, crosslinked polyacrylamide gel was initially used as a sieving matrix[13,14]. When linear hydrophilic polymers were introduced as a replaceable sieving matrix for separation of polynucleotides[15], various polymers were utilized as a sieving matrix for electrophoretic size separation of biopolymers: linear polyacrylamide[16-18], poly(ethylene oxide)[19], dextran[16], guaran[20], glucomannan[21], poly(vinyl alcohol)[22], poly(hydroxypropyl acrylamide)[23], poly(ethoxyethyl acrylamide)[24], agarose[25], and pullulan[26]. Size separations of proteins by capillary electrophoresis were performed mostly by SDS capillary sieving electrophoresis (CSE) in the molecular-weight range between about 14,000 and 205,000. The method was also modified for the size separation of proteins on microchip[27] with poly(dimethyl acrylamide) as a sieving polymer[28]. Capillary electrophoresis meant a number of advantages as compared to electrophoresis in slab gel: faster analysis, automation, higher separation efficiency, and higher detection sensitivity. Nevertheless, a small size of capillaries emphasized the effect of the capillary wall: typically fused silica capillaries were used that contained ionized silanol groups on their internal surface, resulting in strong wall adsorption, significant electroosmotic flow, eddy migration, and consequent mediocre separation efficiency. Electroosmotic flow was eventually suppressed by applying a hydrolytically stable neutral coating on the capillary wall (U.S. Pat. No. 5,143,753). Nevertheless, in SDS CSE, SDS adsorbs on the neutral coating and generates secondary electroosmotic flow. Mediocre reproducibility and separation efficiency are the results of this deleterious effect. Currently, SDS CSE is performed in bare capillaries after extensive rinsing of the capillary between runs, significantly reducing the throughput of the analysis (U.S. Patent Application 20090314638). Hypothetically, electroosmotic flow in SDS CSE could be also suppressed by reducing pH of the sieving medium and a consequent suppression of the silanol ionization in the capillary wall. However, SDS binding of proteins is weaker at pH<6 and SDS electrophoresis at this pH results in significantly broader peaks[29] excluding this alternative from a real world practice.

Anomalous Protein Migration

Anomalous migration of some proteins was observed already in the early years of SDS PAGE when lysozyme and ribonuclease A did not migrate as expected from their molecular weights[1,4,5]. The authors speculated the anomalous proteins did not completely unfold and/or were not saturated with SDS[4]. Later it was found that even a single substitution of a neutral amino acid in α-crystallins resulted in changed mobility in SDS and thus different molecular weight[30]. Electrostatic repulsion between SDS and strongly acidic proteins could have been the cause for lower SDS binding[31]. Also glycoproteins were proposed to bind SDS below its saturation since hydrophilic carbohydrates were not likely to strongly bind SDS. William and Gratzer hypothesized the anomalously slow migration of acidic ferredoxins in SDS PAGE was caused by insufficient surfactant binding due to electrostatic repulsion of SDS and protein carboxylic groups[5]. This idea was corroborated by an observation that some acidic proteins, such as pepsin, papain, and glucose oxidase did not bind measurable amount of SDS[32]. Similarly, maleylation of cyanogen bromide fragments of cytochrome c significantly reduced their apparent molecular weights while that of native cytochrome c was not significantly affected by carbamylation[33]. Lysozyme was also modified by a reaction with dithio-compounds with various charges[4]. Carboxyethyl-, hydroxyethyl-, and aminoethyl-lysozyme derivatives migrated more anodically than lysozyme itself in 8 M urea, in absence of any ionic surfactant. The mobility differences in SDS PAGE indicated the intrinsic charge had an effect on the amount of SDS bound to the proteins.

Guttman and Nolan investigated the accuracy of molecular weights of 65 proteins as determineded by SDS electrophoresis in capillary and slab gel format. Independently of the format, more than one fourth of proteins exhibited biased migration[34].

Normalization of Biased Molecular Weights

It was suggested to use so called Ferguson plot to correct the molecular weight of proteins with biased migration[35,36].

Based on the hypothesis that electrostatic repulsion between ionic surfactant and proteins cause biased migration in electrophoretic size separation, several methods have been tested to normalize protein migration. The anomalously slow migration of acidic ferredoxins in SDS PAGE was normalized by esterification of their carboxyl groups with methanol[5].

Deglycosylation of several glycoproteins with N-glycosidase F improved the accuracy of molecular weights of these glycoproteins in SDS PAGE and SDS CSE on microchip[37].

Several reaction schemes have been used to modify proteins to detect them by laser fluorescence detection. Some of them can be used for sample preparation to normalize protein migration in electrophoresis in the presence of a ionic surfactant.

Modifying Proteins by Carbamylation of Amino Groups

Protein amino groups can be modified by carbamylation with cyanate when homocitrulline is formed[38]

Modifying Proteins on Carboxylic Groups by Reaction with EDC

Proteins can be modified on their carboxylic groups by a reaction with a water-soluble carbodiimide, e.g., 1-ethyl-3-(3-dimethylaminopropyl)carbodiimide (EDC, $(CH_3)_2$—N—$(CH_2)_3$—N=C=N—$CH_2$—$CH_3$). Unstable acylurea ester is formed first then it reacts with a primary amine[38]

The participation of a primary amine in the reaction also means the reaction can be hypothetically used to modify protein amino groups by a reaction with a carboxylic acid and EDC.

Modifying Proteins on Amino Groups by Reaction with Isothiocyanate Derivatives The reaction of protein amino groups with isothiocyanate derivatives has been widely used to label proteins with a fluorescent dye for their laser-induced fluorescence detection in HPLC and other separation methods. Isothiocyanates react with primary amines forming thiourea derivatives[39]

Modifying Proteins on Amino Groups by a Reaction with Succinimidyl Ester Derivatives The reaction of protein amino groups with succinimidyl ester derivatives has been also used for labeling proteins with a fluorescent dye. Succinimidyl ester reacts with primary amines and forms carboxamide derivatives[39]

Modifying Proteins on Amino Groups by a Reaction with Sulfonyl Chloride Derivatives Another reaction of protein amino groups that is to label proteins is with sulfonyl chloride derivatives. Sulfonyl chlorides react with primary amines and form sulfonamide derivatives[39]

Modifying Proteins on Amino Groups by a Reaction with Aldehyde Derivatives The reaction of protein amino groups with aldehyde derivatives has been also used for labeling proteins with a fluorescent dye when a Schiff base is formed first and then it is reduced to a corresponding alkylamine[39]

Modifying Proteins on Sulfhydryl Groups by a Reaction with Charged Dithio Derivatives Proteins can be modified by reaction of their disulfide bridges with dithioderivatives in the presence of an excess thiol, where protein thiols are generated The protein thiols then react with disulfides generating proteins modified in their disulfides[19]

When the modifying disulfide carries a charged moiety the protein intrinsic charge can be also modified[4].

BRIEF SUMMARY OF THE INVENTION

The present invention is suitable for electrophoretic size separation of proteins and particularly sample preparation procedure improving the accuracy of molecular weight determination. Disclosed herein are the compositions of the reagents modifying proteins and the method of the protein modifications improving the accuracy of the protein molecular weights obtained by electrophoretic size separation in the presence of ionic surfactants.

DETAILED DESCRIPTION OF THE INVENTION

We propose to modify proteins during the sample preparation for the electrophoretic size separation and alter their functional groups and so suppress the existing charged groups. Moreover, these modifications reverse the sign of the charge of the charged groups and thus make a complex formation between proteins and ionic surfactant easier. Similarly we disclose modification of glycoproteins when the carbohydrate component is oxidized with periodate.

We disclose here a protein denaturing composition for sample preparation of proteins prior their electrophoretic size separation, consisting of:
a) an ionic surfactant,
b) an electrolyte,
c) a reducing reagent cleaving disulfidic bridges,
d) a mobility modifier that reacts with proteins and changes the electrophoretic mobility of the complex between said protein and said ionic surfactant.

Said ionic surfactant is selected from the group of surfactants consisting of sodium dodecylsulfate, lithium dodecylsulfate, sodium tetradecylsulfate, sodium N-lauroylsarcosinate, hexadecyltrimethylammonium bromide, hexadecyltrimethylammonium chloride, hexadecyldimethylethylammonium bromide, octadecyltrimethylammonium bromide, tetradecyltrimethylammonium bromide, and dodecyltrimethylammonium bromide.

Said electrolyte is selected from the group of electrolytes consisting of potassium chloride, potassium phosphate, potassium acetate, potassium sulfate, potassium nitrate, potassium cyanate, ammonium chloride, ammonium phosphate, ammonium acetate, ammonium sulfate, ammonium nitrate, sodium chloride, sodium phosphate, sodium acetate, sodium sulfate, sodium nitrate, sodium borate, Tris hydrochloride, ethanolamine hydrochloride, diethanolamine hydrochloride, triethanolamine hydrochloride, Bis-Tris-Propane hydrochloride, Bis-Tris hydrochloride, methylglucamine hydrochloride, ethylenediamine hydrochloride, tetramethylethylenediamine hydrochloride, and aminomethylpropanediol hydrochloride.

Said reducing reagent cleaving disulfidic bridges is selected from the group of compounds consisting of mercaptoethanol, dithiothreitol, dithioerythriol, tris(carboxyethyl)phosphine, thioacetic acid, thiopropionic acid, and cysteamine.

Said mobility modifier is selected from the group of reagents consisting of
i. 1-ethyl-3-(3-dimethylaminopropyl)carbodiimide hydrochloride,
ii. acetic anhydride, aconitic anhydride, citraconic anhydride, phtalic anhydride, succinic anhydride, glutaric anhydride, itaconic anhydride, propionic anhydride,
iii. salt of periodic acid, particularly sodium periodate,
iv. salt of cyanic acid particularly potassium cyanate, salt of sulfocyanic acid,
v. dithiodialkylcarboxylic acid particularly dithiodiglycolic acid, dithiodipropionic acid, and dithiodibenzoic acid, also dithiodialkylamine,
vi. low-fluorescence isothiocyanate, particularly sulfophenyl isothiocyanate, carboxyphenyl isothiocyanate, disulfophenyl isothiocyanate, trisulfophenyl isothiocyanate, and dicarboxyphenyl isothiocyanate,
vii. low-fluorescence succinimidyl ester,
viii. low-fluorescence sulfonyl chloride,
ix. low-fluorescence dichlorotriazine,
x. low-fluorescence tetrafluorophenylester.

Specifically we disclose a protein denaturing composition consisting of about 0.1 M potassium cyanate, about 1% hexadecyltrimethylammonium chloride, and about 1% tris(carboxyethyl)phosphine and also a protein denaturing composition consisting of about 0.1 M sodium periodate, about 1% hexadecyltrimethylammonium chloride, about 1% tris(carboxyethyl)phosphine, and about 100 mM sodium acetate. We further disclose a protein denaturing composition consisting of about 0.1 M sodium thioglycolate, about 1% hexadecyltrimethylammonium chloride, and about 10 mM tris(carboxyethyl)phosphine. We also disclose a protein denaturing composition consisting of about 0.1 M potassium cyanate, about 1% sodium dodecylsulfate, and about 1% dithiotreitol. We also disclose a protein denaturing composition consisting of about 0.1 M sodium periodate, about 1% sodium dodecylsulfate, about 1% dithiotreitol, and about 100 mM sodium acetate.

Further we disclose a method for denaturation and sample preparation of proteins prior to their size separation by electrophoresis, consisting of the steps: mixing the protein sample with an ionic surfactant, electrolyte, reducing reagent cleaving disulfidic bridges, and mobility modifier that reacts with proteins and changes the electrophoretic mobility of the complex between said protein and said ionic surfactant; said mobility modifier is selected from the group of reagents consisting of 1-ethyl-3-(3-dimethylaminopropyl)carbodiimide hydrochloride, acetic anhydride, aconitic anhydride, citraconic anhydride, phtalic anhydride, succinic anhydride, glutaric anhydride, itaconic anhydride, propionic anhydride, a salt of periodic acid, particularly sodium periodate, a salt of cyanic acid, particularly potassium cyanate, a salt of sulfocyanic acid, dithiodialkylcarboxylic acid, dithiodialkylamine, low-fluorescence isothiocyanate, low-fluorescence succinimidyl ester, low-fluorescence sulfonyl chloride, low-fluorescence dichlorotriazine, low-fluorescence tetrafluorophenylester, and heating the prepared mixture at 40° C.-100° C. for 1-60 min.

We also disclose a method for capillary sieving electrophoresis with cationic surfactant for size separation of proteins, consisting of the steps: a) Preparing a protein sample by reacting the protein with the protein mobility modifier, said mobility modifier selected from the group of reagents consisting of 1-ethyl-3-(3-dimethylaminopropyl)carbodiimide hydrochloride, acetic anhydride, aconitic anhydride, citraconic anhydride, phtalic anhydride, succinic anhydride, glutaric anhydride, itaconic anhydride, propionic anhydride, salt of periodic acid, particularly sodium periodate, salt of cyanic acid, particularly potassium cyanate, salt of sulfocyanic acid, dithiodialkylcarboxylic acid, dithiodialkylamine, low-fluorescence isothiocyanate, low-fluorescence succinimidyl ester, low-fluorescence sulfonyl chloride, low-fluorescence dichlorotriazine, low-fluorescence tetrafluorophenylester, b) rinsing the separation capillary; c) filling the capillary with a separation medium for capillary electrophoretic size separation of proteins, said separation medium consisting essentially of a cationic surfactant; an acidic buffer; and a sieving polymer, wherein said sieving polymer is selected from the group consisting of linear polyacrylamide, poly(dimethyl acrylamide), poly(hydroxyethyl acrylamide), poly(hydroxypropyl acrylamide), poly(ethoxyethyl acrylamide), poly(vinyl alcohol), poly(vinyl pyrrolidone), hydroxyethyl cellulose, scleroglucan, guaran, locust bean gum, glucomannan, pullulan, dextran, and poly(ethylene oxide), with a proviso that when said sieving polymer is poly(ethylene oxide), it is in the concentration from about 16 g/L to about 60 g/L; d) Sample injection, wherein the capillary inlet is washed by a triple immersion in distilled water, then the capillary inlet and cathode are immersed in the sample, capillary outlet and anode are immersed in a vial containing separation medium, and an injection voltage from about 0.5 kV to about 12 kV is applied between the anode and cathode for about 1 s to about 60 s; e) separation, wherein the capillary inlet and cathode are immersed in a vial containing said separation medium, capillary outlet and anode are immersed in other vial containing said separation medium, then a separation voltage from about 1 kV to about 20 kV being applied between the anode and cathode for about 1 minute to about 20 minutes; f) detection, wherein absorption of monochromatic light having wavelength from about 210 nm to about 420 nm is measured and plotted in electropherogram for further data analysis.

EXAMPLES

The separations described in these examples were performed in 3D CE capillary electrophoresis instrument at 20° C. in a bare or coated capillary of internal diameter 75 μm and outer diameter 360 μm with UV detection at 214 nm or 420 nm

Example 1

Carbamylation of Cytochrome c for an Improved Accuracy of Molecular Weights by Capillary Sieving Electrophoresis with Cationic Surfactant 5 mg bovine heart cytochrome c was dissolved in 820 μL water and mixed with 40 μL of 25% cetyltrimethylammonium chloride, 40 μL of 10% tricarboxyethyl phosphine, and 100 μL of 1 M KCNO. After dissolving, the mixture was heated at 70° C. for 20 min and then cooled to room temperature.

Example 2

Oxidation of Ovalbumin with $NaIO_4$ for an Improved Accuracy of Molecular Weights by Capillary Sieving Electrophoresis with Cationic Surfactant 5 mg of ovalbumin was dissolved in 1 mL of 0.1 M sodium acetate buffer, pH 5.5 and mixed with 75 μL of 0.2 M $NaIO_4$ and 50 μL of 25% cetyltrimethylammonium chloride. The mixture was heated at 40° C. for 10 min. Then 50 μL of 50% glycerol was added.

Example 3

Capillary Electrophoresis of Carbamylated Cytochrome c

Figure 1:
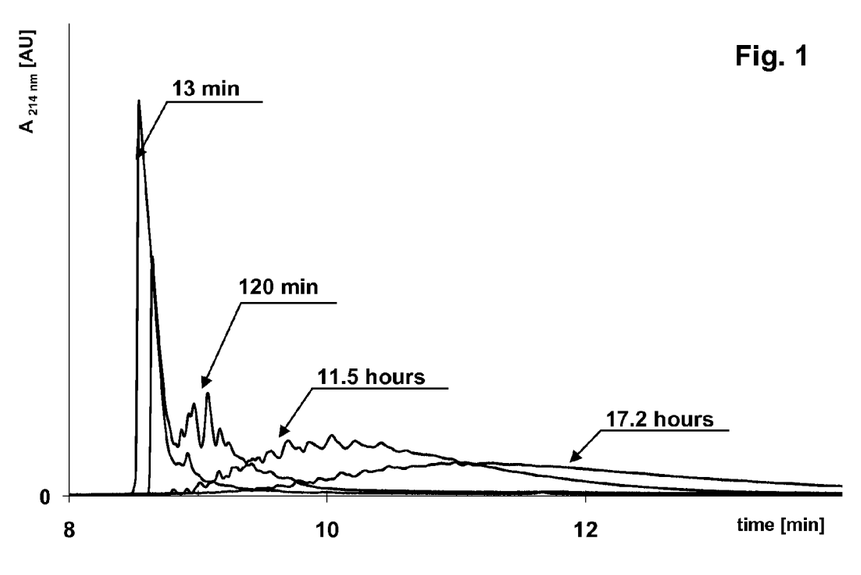
FIG. 1 shows CZE profile of carbamylated cytochrome c during the time course of the reaction. Separation medium: 100 mM β-alanine, 100 mM citric acid. Coated capillary: iCap™ (Alcor BioSeparations, Palo Alto, Calif. U.S.A.), total length=335 mm, effective length=250 mm, ID=50 µm, OD=360 µm. Voltage: +10 kV. Detection: UV absorption at 214 nm. Pressure injection: 3 s at 50 mbar. Sample: 5 g/L cytochrome c in 100 mM KCNO, reaction performed at room temperature.

Carbamylated cytochrome c prepared by the procedure in Example 1 was analyzed by capillary electrophoresis in a coated capillary (U.S. Pat. No. 7,799,195) 50 μm ID, 360 μm OD, total length 335 mm, effective length 250 mm. First the capillary was flushed with distilled water then it was filled with 100 mM β-alanine citrate, pH 3.3. Carbamylated cytochrome c was injected electrokinetically at +5 kV for 10 s and separated at +10 kV for 30 min. Cytochrome c was detected by measuring light adsorption at 214 nm or 420 nm (FIG. 1).

Example 4

Figure 2:
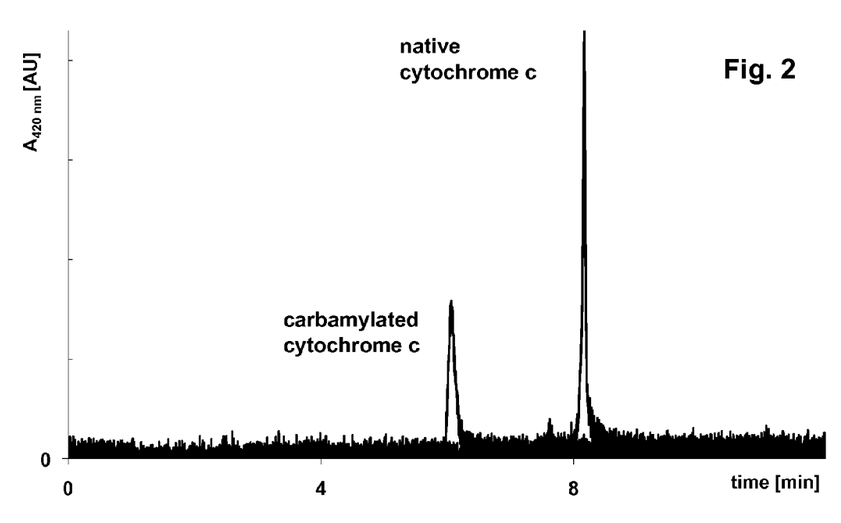
FIG. 2 shows migration of carbamylated and non-carbamylated cytochrome c in capillary sieving electrophoresis with cationic surfactant. Separation medium: 100 mM β-alanine, 100 mM glutamic acid, 0.2% CTAC, 18 g/L poly(ethylene oxide) ($M_w$ 600,000). Capillary: bare capillary, $l_{total}$=335 mm, $l_{effective}$=250 mm, ID=75 µm, OD=360 µm. Voltage: +10 kV. Electrokinetic injection: 15 s at +8 kV. Sample: 5 g/L cytochrome c in 10 g/L CTAC, 100 mM KCNO, 0.4% tris(carboxyethyl)phosphine hydrochloride. Detection by light absorption at 420 nm.
Figure 3:
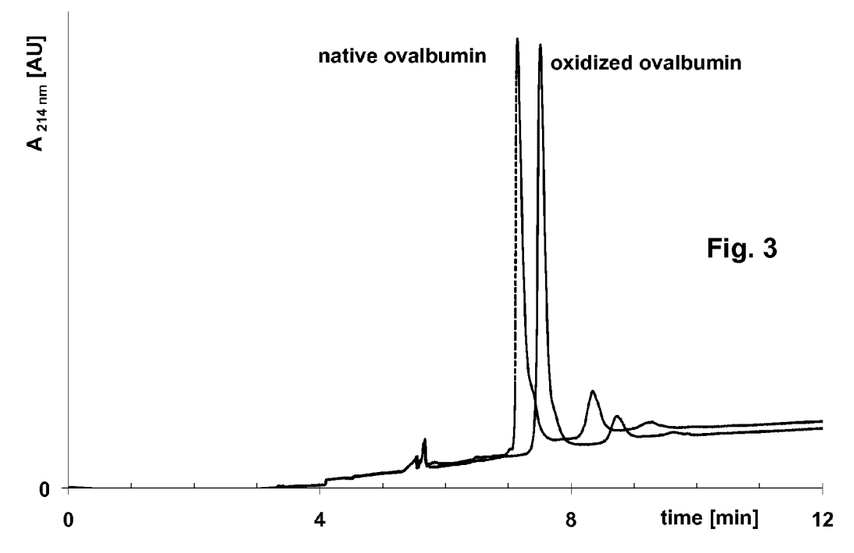
FIG. 3 compares the electropherograms of ovalbumin and $NaIO_4$-treated ovalbumin in capillary sieving electrophoresis with cationic surfactant. Separation medium: 100 mM β-alanine, 100 mM 2-hydroxyisobutyric acid, 2 g/L CTAC, 18 g/L poly(ethylene oxide) ($M_w$ 600,000). Capillary: bare capillary, l(total)=335 mm, l(effective)=250 mm, ID=75 µm, OD=360 µm. Voltage: +10 kV. Electrokinetic injection: 15 s at +8 kV. Sample: 5 mg ovalbumin in 1 mL of 0.1 M acetate buffer, pH 5.5, 75 µL of water (for native ovalbumin) or 75 µL of 0.2 M $NaIO_4$ (for oxidized ovalbumin) in 0.1 M acetate buffer, and 50 µL of 25% CTAC were added. After 10 min incubation at 40° C., the remaining periodate was quenched with 50 µL of 50% glycerol.

Analysis of Proteins by Capillary Sieving Electrophoresis with a Cationic Surfactant Capillary sieving electrophoresis with a cationic surfactant of proteins was performed in a bare capillary 75 μm ID, 360

μm OD, total length 335 mm, effective length 250 mm. The capillary was flushed with distilled water and filled with a composition containing 16 g/L polyethylene oxide ($M_w$, 600 k), 100 mM β-alanine glutamate, 0.2% cetyltrimethylammonium chloride. Proteins were injected electrokinetically at +8 kV for 15 s, separated at +10 kV for 20 min, and detected by UV adsorption at 214 nm (FIGS. 2 and 3). Modified proteins showed changed migration mobility.

Example 5

Figure 4:
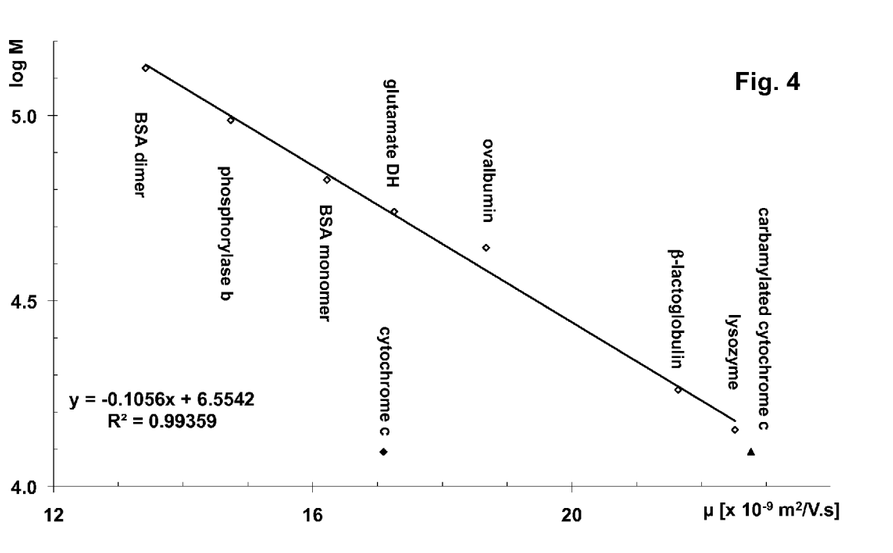
FIG. 4 shows the relation between logarithmic molecular weight of proteins and their electrophoretic mobilities. ◆-cytochrome c, ▲-carbamylated cytochrome c. Experimental conditions were same as described in FIG. 2.

Molecular Weight of Proteins Determined by Capillary Sieving Electrophoresis with a Cationic Surfactant Protein mobilities μ were calculated from equation (1)

$$\mu = \frac{L_t \times L_{eff}}{V \times t_m} \quad (1)$$

where $L_t$ is the total capillary length, $L_{eff}$ is the effective capillary length, V is the applied voltage and $t_m$ is the migration time of protein. Logarithmic molecular weights of proteins were plotted against the calculated mobilities. Using suitable proteins as molecular weight standards, a calibration curve was plotted (FIG. 4) and an equation, which describes the plot, was used to calculate the apparent molecular weights of the tested proteins. Cytochrome c with a true molecular weight 12,400 exhibited apparent molecular weight of 56,200, i.e., the error of the molecular weight was about 350% whereas the carbamylated cytochrome c, having approximately the same true molecular weight, showed the apparent molecular weight of 12,100, which corresponds to a relative error of −2.3%.

Example 6

Figure 5:
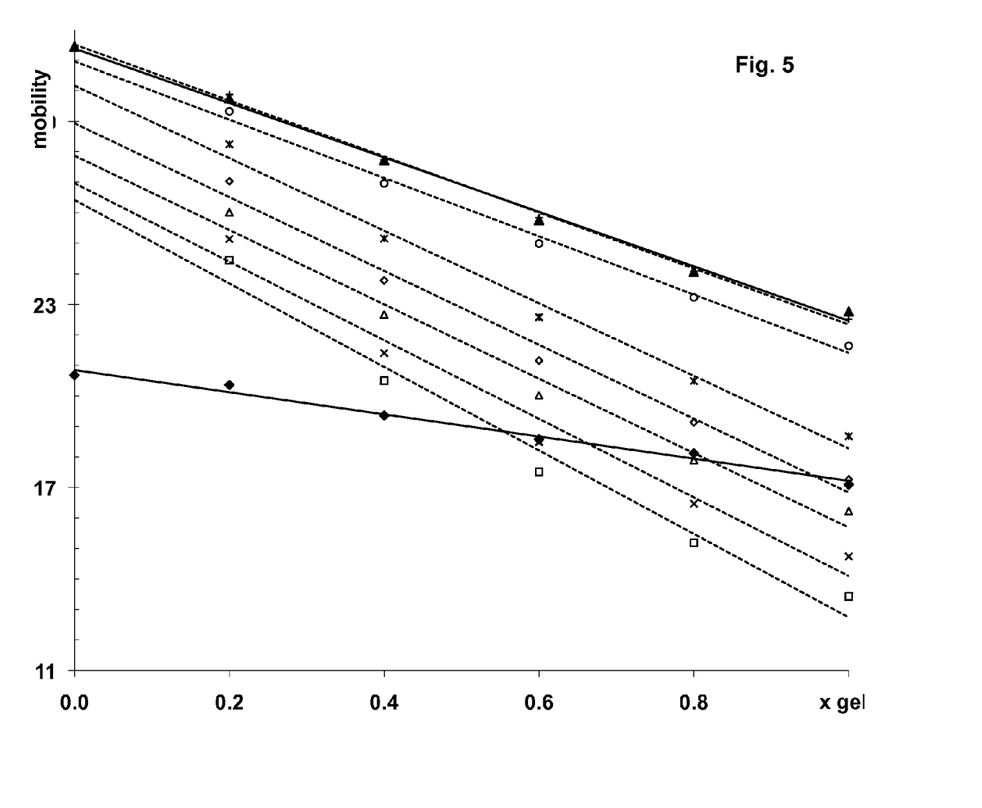
FIG. 5 displays the Ferguson plot for molecular weight standards and native and carbamylated cytochrome c. +-lysozyme, ○-β-lactoglobulin, ※-ovalbumin, ◇-glutamate dehydrogenase, △-BSA (monomer), x-phosphorylase b, □-BSA dimer, ◆-cytochrome c, ▲-carbamylated cytochrome c. Experimental conditions were same as described in FIG. 2.

Ferguson Plot for Proteins Separated by Capillary Sieving Electrophoresis with a Cationic Surfactant To measure the dependence of protein mobilities on the concentration of the sieving polymer in capillary sieving electrophoresis with a cationic surfactant, the electrophoretic separation was performed in 0-16 g/L polyethylene oxide ($M_w$, 600 k), 100 mM β-alanine glutamate, 0.2% cetyltrimethylammonium chloride. A bare capillary, 75 μm ID, 360 μm OD, total length 335 mm, effective length 250 mm, was flushed with distilled water and filled with a composition containing 0-16 g/L polyethylene oxide ($M_w$, 600 k), 100 mM β-alanine glutamate, 0.2% cetyltrimethylammonium chloride. Proteins were injected electrokinetically at +8 kV for 15 s, separated at +10 kV for 20 min, and detected by UV adsorption at 214 nm. The protein mobilities μ were calculated from the equation 1 and plotted in the Ferguson plot as a function of the sieving polymer concentration (FIG. 5). The Ferguson plot showed the anomalous migration of native cytochrome c and the proper migration of carbamylated cytochrome c.

The invention claimed is:

1. A protein denaturing composition for sample preparation of proteins prior to their electrophoretic size separation, consisting of:
   a) an ionic surfactant;
   b) an electrolyte;
   c) a reducing reagent cleaving disulfidic bridges; and
   d) a mobility modifier that reacts with proteins and changes the electrophoretic mobility of a complex between said protein and said ionic surfactant; wherein said mobility modifier is selected from the group consisting of
   a salt of periodic acid;
   a salt of cyanic acid, and a salt of sulfocyanic acid.

2. A protein denaturing composition of claim 1, wherein said ionic surfactant is selected from the group of surfactants consisting of sodium dodecylsulfate, lithium dodecylsulfate, sodium tetradecylsulfate, sodium N-lauroylsarcosinate, hexadecyltrimethylammonium bromide, hexadecyltrimethylammonium chloride, hexadecyldimethylethylammonium bromide, octadecyltrimethylammonium bromide, tetradecyltrimethylammonium bromide, and dodecyltrimethylammonium bromide.

3. A protein denaturing composition of claim 1, wherein said electrolyte is selected from the group of electrolytes consisting of potassium chloride, potassium phosphate, potassium acetate, potassium nitrate, potassium cyanate, ammonium chloride, ammonium phosphate, ammonium acetate, ammonium sulfate, ammonium nitrate, sodium chloride, sodium phosphate, sodium acetate, sodium sulfate, sodium nitrate, Tris hydrochloride, ethanolamine hydrochloride, diethanolamine hydrochloride, triethanolamine hydrochloride, Bis-Tris-Propane hydrochloride, Bis-Tris hydrochloride, methylglucamine hydrochloride, ethylenediamine hydrochloride, tetramethylethylenediamine hydrochloride, and aminomethylpropanediol hydrochloride.

4. A protein denaturing composition of claim 1, wherein said reducing reagent cleaving disulfidic bridges is selected from the group of compounds consisting of mercaptoethanol, dithiotreitol, dithioerythriol, tris(carboxyethyl)phosphine, thioacetic acid, thiopropionic acid, and cysteamine.

5. A protein denaturing composition of claim 1, wherein said salt of periodic acid is sodium periodate.

6. A protein denaturing composition of claim 1, wherein said salt of cyanic acid is potassium cyanate.

7. A protein denaturing composition of claim 1, wherein said protein denaturing composition consists of about 0.1 M potassium cyanate, about 1% hexadecyltrimethylammonium chloride, and about 10 mM tris(carboxyethyl)phosphine.

8. A protein denaturing composition of claim 1, wherein said protein denaturing composition consists of about 0.1 M sodium thioglycolate, about 1% hexadecyltrimethylammonium chloride, and about 10 mM tris(carboxyethyl)phosphine.

9. A protein denaturing composition of claim 1, wherein said protein denaturing composition consists of about 0.1 M potassium cyanate, about 1% sodium dodecylsulfate, and about 1% dithiotreitol.

10. A protein denaturing composition of claim 1, wherein said protein denaturing composition comprises about 0.1 M sodium periodate, about 1% hexadecyltrimethylammonium chloride, about 10 mM tris(carboxyethyl)phosphine, and about 100 mM sodium acetate.

11. A protein denaturing composition of claim 1, wherein said protein denaturing composition comprises about 0.1 M sodium periodate, about 1% sodium dodecylsulfate, about 1% dithiotreitol, and about 100 mM sodium acetate.

12. A method for denaturation and sample preparation of proteins prior to their size separation by electrophoresis, consisting of the steps:
   a) preparing a protein sample by mixing it with
   an ionic surfactant;
   an electrolyte;
   a reducing reagent cleaving disulfidic bridges; and a mobility modifier that reacts with proteins and changes the electrophoretic mobility of a complex between said protein and said ionic surfactant; wherein said mobility modifier is selected from the group consisting of a salt of periodic acid;

a salt of cyanic acid, and a salt of sulfocyanic acid, and b) heating the sample at 40° C. -100° C. for 1-60 min.

13. A method for sample preparation of proteins of claim 12, wherein said mobility modifier is potassium cyanate.

14. A method for sample preparation of proteins of claim 12, wherein said mobility modifier is sodium periodate.

15. A method for electrophoretic size separation of proteins, consisting of the steps:

Preparing the protein sample by the method of claim 12 b) sample application c) protein separation by migration in a sieving medium in electric field; and d) detection.

16. A method for electrophoretic size separation of proteins, wherein said proteins are separated by capillary sieving electrophoresis with a cationic surfactant, consisting of the steps:

a) preparing a protein sample by heating a protein solution at 40° C. -100° C. for 1-60 min with about 1% cetyltrimethylammonium chloride, about 1% tris(carboxyethyl)phosphine, and a protein mobility modifier, wherein said mobility modifier is selected from the group consisting of a salt of periodic acid;

a salt of cyanic acid and a salt of sulfocyanic acid;

b) rinsing a separation capillary;

c) filling the capillary with a separation medium for capillary electrophoretic size separation of proteins, said separation medium consisting of:

i) a cationic surfactant;

ii) an acidic buffer; and iii) a sieving polymer, wherein said sieving polymer is selected from the group consisting of linear polyacrylamide, poly(dimethyl acrylamide), poly(hydroxyethyl acrylamide), poly(hydroxypropyl acrylamide), poly (ethoxyethyl acrylamide), poly(vinyl alcohol), poly(vinyl pyrrolidone), hydroxyethyl cellulose, scleroglucan, guaran, locust bean gum, glucomannan, pullulan, dextran, and poly(ethylene oxide), with a proviso that when said sieving polymer is poly(ethylene oxide), it is in the concentration from about 16 g/L to about 60 g/L;

d) injecting the sample, wherein a capillary inlet is washed by a triple immersion in distilled water, then the capillary inlet and cathode are immersed in the sample, capillary outlet and anode are immersed in a vial containing separation medium, and finally an injection voltage from about 0.5 kV to about 12 kV is applied between the anode and cathode for about 1 s to about 60 s;

e) separating, wherein the capillary inlet and cathode are immersed in a vial containing said separation medium, capillary outlet and anode are immersed in other vial containing said separation medium, then a separation voltage from about 1 kV to about 20 kV is applied between the anode and cathode for about 1 minute to about 20 minutes; and f) detecting, wherein absorption of monochromatic light having wavelength from about 210 nm to about 420 nm is measured and plotted in electropherogram for further data analysis.

17. A method for capillary sieving electrophoresis with cationic surfactant of claim 16, wherein said mobility modifier is about 100 mM potassium cyanate.

18. A method for capillary sieving electrophoresis with cationic surfactant of claim 16, wherein said mobility modifier is about 100 mM sodium periodate.

* * * * *